(12) United States Patent
Geiger et al.

(10) Patent No.: US 11,678,845 B2
(45) Date of Patent: Jun. 20, 2023

(54) MULTI-MODALITY HARNESS

(71) Applicant: NuVasive, Inc., San Diego, CA (US)

(72) Inventors: D. J. Geiger, San Diego, CA (US);
Chris Ryan, San Diego, CA (US);
Richard W. Schermerhorn, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 769 days.

(21) Appl. No.: 16/688,737

(22) Filed: Nov. 19, 2019

(65) Prior Publication Data
US 2021/0145364 A1    May 20, 2021

(51) Int. Cl.
*A61B 5/00* (2006.01)
*A61B 5/389* (2021.01)
*A61N 1/04* (2006.01)

(52) U.S. Cl.
CPC ............ *A61B 5/6831* (2013.01); *A61B 5/389* (2021.01); *A61B 2505/05* (2013.01); *A61B 2560/0443* (2013.01); *A61B 2560/0475* (2013.01); *A61B 2562/222* (2013.01); *A61B 2562/227* (2013.01); *A61N 1/0452* (2013.01)

(58) Field of Classification Search
CPC ... A61B 5/6831; A61B 5/389; A61B 2505/05; A61B 2560/0443; A61B 2560/0475; A61B 2562/222; A61B 2562/227; A61B 5/273; A61B 5/296; A61N 1/0452
See application file for complete search history.

(56) References Cited

U.S. PATENT DOCUMENTS

| | | | | |
|---|---|---|---|---|
| 4,632,121 | A * | 12/1986 | Johnson | A61B 5/303 439/502 |
| 6,938,927 | B1 * | 9/2005 | Martin | A63C 11/221 135/69 |
| 2016/0278649 | A1 * | 9/2016 | Gharib | A61B 34/20 |
| 2019/0313973 | A1 * | 10/2019 | Harada | A61B 5/374 |

* cited by examiner

*Primary Examiner* — Eric F Winakur
*Assistant Examiner* — Abid A Mustansir
(74) *Attorney, Agent, or Firm* — Merchant & Gould P.C.

(57) ABSTRACT

A harness comprising a patient module connector, an extremity hub; a cable branch including a plurality of channel pairs. The cable branch includes a first end coupled to the patient module connector and a second end coupled to the extremity hub. The harness comprises a monitoring cable configured to attach and detach from the extremity hub.

12 Claims, 9 Drawing Sheets

MULTI-MODALITY HARNESS

FIELD

This disclosure describes a harness and a monitoring cable for use during a surgical procedure.

BACKGROUND

Electromyography (EMG) is the study of the electrical activity of muscles. It is a test used to help assess the health and function of nerves and/or muscles. EMG can be used by a surgeon to assess proper pedicle screw placement in fusion surgeries to help reduce the chance of nerve damage, or to aid in assessing nerve proximity and location during surgical approaches. Typically, one or more hardware and software components are used to assist in performing an EMG test during a surgical procedure.

SUMMARY

In one embodiment, a harness comprises a patient module connector, an extremity hub, a cable branch including a plurality of channel pairs. The cable branch includes a first end coupled to the patient module connector and a second end coupled to the extremity hub. The harness comprises a monitoring cable configured to attach and detach from the extremity hub. The monitoring cable includes a first electrode wire, a second electrode wire, and a housing. The housing is configured to receive a first end of the first electrode wire and a first end of the second electrode wire. The housing includes a first aperture and a second aperture along an axis of the housing. The monitoring cable includes a body that includes a channel formed by an aperture along a first axis of the body. The channel includes a first retention element located on a first surface of the channel and along a second axis of the body. The channel includes a second retention element located along a second surface of the channel and along the second axis. The first axis and the second axis are perpendicular. The body is configured to slidably receive the housing. The housing is held in a fixed position based on insertion of the first retention element within the first aperture and insertion of the second retention element within the second aperture.

In another embodiment, a monitoring cable comprises a first electrode wire, a second electrode wire, and a housing. The housing is configured to receive a first end of the first electrode wire and a first end of the second electrode wire. The housing includes a first aperture and a second aperture along an axis of the housing. The monitoring cable comprises a body. The body includes a channel formed by an aperture along a first axis of the body. The channel includes a first retention element located on a first surface of the channel and along a second axis of the body. The aperture includes a second retention element located along a second surface of the channel and along the second axis. The first axis and the second axis are perpendicular. The body is configured to slidably receive the housing. The housing is held in a fixed position based on insertion of the first retention element within the first aperture and insertion of the second retention element within the second aperture.

In another embodiment, a harness comprises a patient module connector, an extremity hub, and a cable branch including a plurality of channel pairs. The cable branch includes a first end coupled to the patient module connector and a second end coupled to the extremity hub. The harness includes a monitoring cable. The monitoring cable is configured to attach and detach from the extremity hub. The monitoring cable includes a plurality of electrode wires and a plurality of housings configured to receive the plurality of electrode wires. The plurality of housings includes a plurality of apertures. The monitoring cable includes a body. The body includes a plurality of channels formed by a plurality of apertures along the body. The plurality of channels include a plurality of retention elements located on surfaces of the plurality of channels. The body is configured to slidably receive the plurality of housings and hold the plurality of housings in fixed positions based on insertion of the plurality of retention elements within the plurality of apertures.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
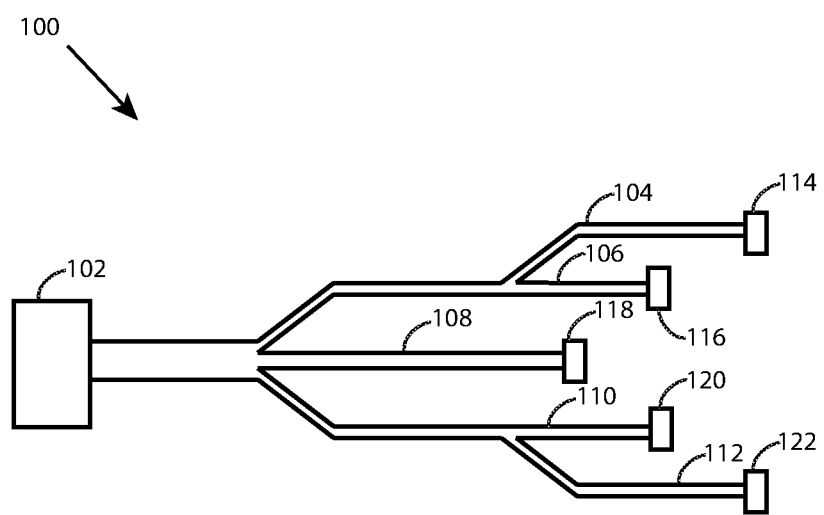
FIG. 1 illustrates an example harness for performing a surgical procedure, according to an embodiment of the present disclosure.

Illustrative embodiments of the invention are described below. In the interest of clarity, not all features of an actual implementation are described in this specification. It will of course be appreciated that in the development of any such actual embodiment, numerous implementation-specific decisions must be made to active the developers' specific goals, such as compliance with system-related and businessrelated constraints, which will vary from one implementation to another. Moreover, it will be appreciated that such a development effort might be complex and time-consuming, but nevertheless be a routine undertaking for those of ordinary skill in the art having the benefit of this disclosure. It is furthermore to be readily understood that, although discussed below primarily within the context of spinal surgery, the systems and methods of the present invention may be employed in any number of anatomical settings to provide access to any number of different surgical target sites throughout the body.

Examples described herein include a harness and a monitoring cable for performing a surgical procedure. In one example, a harness for use during a surgical procedure includes a patient module connector. The patient module connector is configured to connect to a monitoring system for providing various neurophysiologic assessments during the surgical procedure. The harness also includes an extremity hub. The extremity hub includes one or more connectors for mating with one or more wires connected to one or more electrodes. The harness also includes a cable branch including a plurality of channel pairs. The plurality of channel pairs are configured for providing one or more stimulation signals to various locations of a body of a patient during the surgical procedure. The plurality of channel pairs are also configured for acquiring one or more responses based on the one or more stimulation signals. In one example, the responses are provided to the monitoring system for analysis and for providing feedback to a user during the surgical procedure. In one example, the cable branch includes a first end coupled to the patient module connector and a second end coupled to the extremity hub. In another example, the harness includes multiple cable branches that are also coupled to the patient module connector and the extremity hub as described herein.

The harness also includes a monitoring cable configured to attach and detach from the extremity hub. In one example, the monitoring cable includes at least a first electrode wire and a second electrode wire. The monitoring cable also includes a housing that is integrally molded to receive a first end of the first electrode wire and a first end of the second electrode wire. In one embodiment, the housing includes a first aperture and a second aperture along an axis of the housing. In another embodiment, the housing includes additional apertures along one or more axes of the housing. The monitoring cable also includes a body that includes an aperture along a first axis of the body. The aperture includes a first retention element located on a first surface of the aperture and along a second axis of the body. The aperture also includes a second retention element along a second surface of the aperture and along the second axis. In one embodiment, the first axis and the second axis are perpendicular. The body of the monitoring cable is configured to slidably receive the housing. The body is held in a fixed position based on insertion of the first retention element within the first aperture and insertion of the second retention element within the second aperture.

Referring now to the figures, FIG. 1 is a diagram of an example harness 100 for performing a surgical procedure. The example harness 100 includes a patient module connector 102, cable branches 104, 106, 108, 110, and 112, and extremity hubs 114, 116, 118, 120, and 122.

The patient module connector 102 includes a connection point to a patient module (not shown). In one example, the patient module connector 102 includes 70 distinct channels. Continuing with this example, the patient module connector 102 includes a programmable memory device. In one example, the programmable memory device is an electrically erasable programmable read-only memory. In one example, there are numerous stimulation channels for providing a stimulation signal to the body of a patient during a surgical procedure and numerous acquisition channels for acquiring a response to a stimulation signal provided to the body of the patient.

The cable branches 104, 106, 108, 110, and 112 are designed to utilize the same cable construction. In one example, the cable branch 104 includes six acquisition channel pairs and one stimulation channel pair. Continuing with this example, the insulation surrounding the stimulation channel pair needs to ensure 1500 VAC isolation between the six channel acquisition channel pairs. In one example, cable branches 106, 110, and 112 are configured in a similar manner as described above with regard to cable branch 104. In this example, cable branch 108 has an inverted layout that includes one acquisition channel pair, five stimulation channel pairs, and one channel pair for ground.

The extremity hubs 114, 116, 118, 120, and 122 are designed to utilize the same overmold design. The same overmold design enables the extremity hubs to use the same tool. This also optimizes manufacturing costs as well as ensuring a reproducible design. In one example, the extremity hubs 114, 116, 120, and 122 have the same connector layout.

Figure 2:
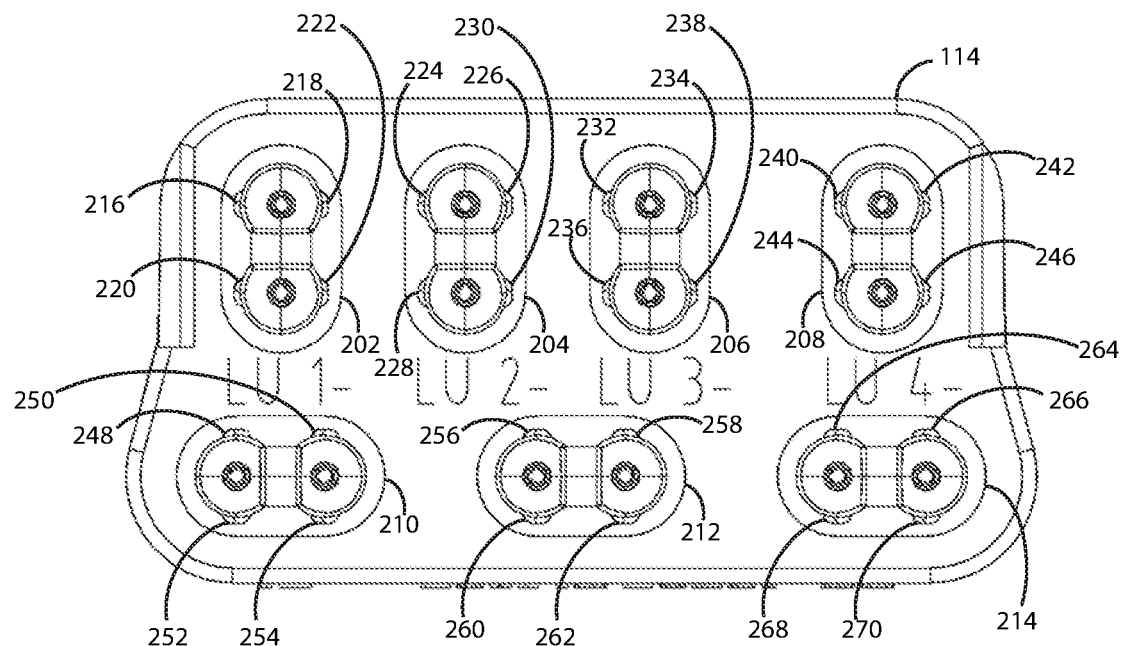
FIG. 2 illustrates an example extremity hub of FIG. 1 for performing a surgical procedure, according to an embodiment of the present disclosure.

FIG. 2 illustrates a front view of the extremity hub 114 of FIG. 1. As shown in FIG. 2, the extremity hub 114 includes seven pairs of dual connector female receptacles 202, 204, 206, 208, 210, 212, and 214. There are four dual connector female receptacles 202, 204, 206, and 208 in a vertical orientation along a first axis of the extremity hub 114 and three dual connector female receptacles 210, 212, and 214 in a horizontal orientation along a second axis of the extremity hub 114. As shown in FIG. 2, the dual connector female receptacle 202 includes retention elements 216, 218, 220, and 222. The dual connector female receptacle 204 includes retention elements 224, 226, 228, and 230. The dual connector female receptacle 206 includes retention elements 232, 234, 236, and 238. The dual connector female receptacle 208 includes retention elements 240, 242, 244, and 246. The dual connector female receptacle 210 includes retention elements 248, 250, 252, and 254. The dual connector female receptacle 212 includes retention elements 256, 258, 260, and 262. The dual connector female receptacle 214 includes retention elements 264, 266, 268, and 270. In one example, the extremity hubs 116, 120, and 122 the same connector layout to the connector layout of extremity hub 114. In one example, the extremity hub 118 has a similar connector layout to the connector layouts of extremity hubs 114, 116, 120, and 122 except for two of the dual female connector receptacles along the second axis.

Figure 3:
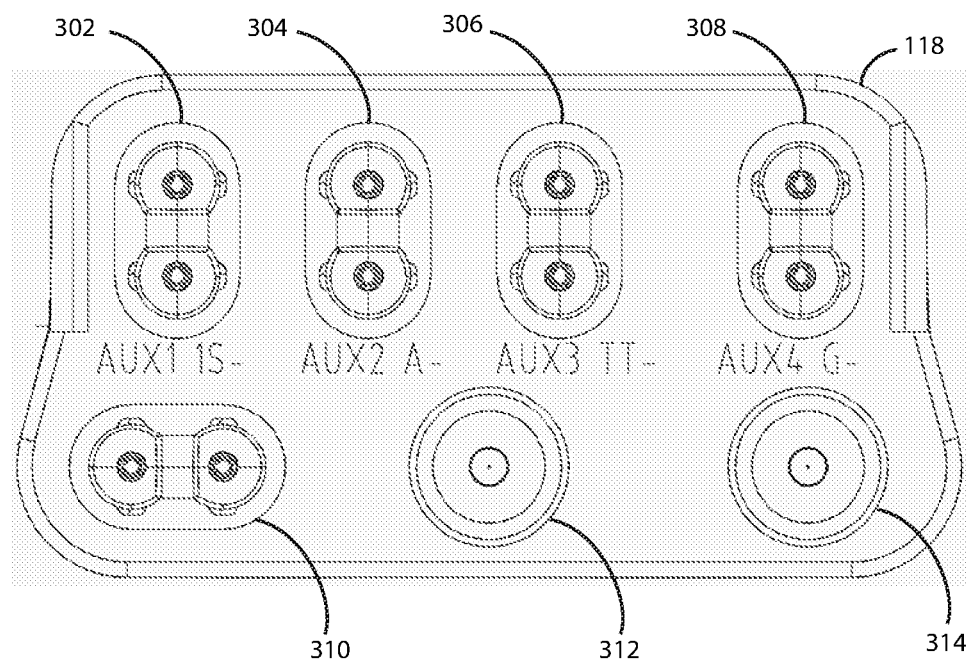
FIG. 3 illustrates another example extremity hub of FIG. 1 for performing a surgical procedure, according to an embodiment of the present disclosure.

FIG. 3 illustrates a front view of the extremity hub 118 of FIG. 1. As shown in FIG. 3, the extremity hub 118 includes five pairs of dual connector female receptacles 302, 304, 306, 308, and 310. In place of the other two dual female connector receptacles of the extremity hub 114, the extremity hub 118 includes a pair of Deutsches Institut für Normung (DIN) connections points 312 and 314. In one example, the DIN connection points provide connection points for motor evoked potential (MEP) cranial stimulation leads. In another example, the DIN connection points provide connection points for transabdominal stimulation and generation of transabdominal muscle action potentials.

Figure 4:
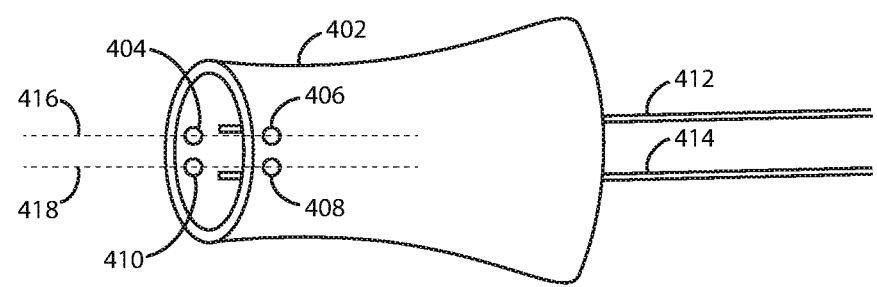
FIG. 4 illustrates an example housing for performing a surgical procedure, according to an embodiment of the present disclosure.

FIG. 4 illustrates an example housing 402 that includes an electrode. The housing 402 includes apertures 404, 406, 408, and 410. The housing 402 also is integrally formed with electrode wires 412 and 414. The housing 402 includes apertures 404 and 406 along an axis 416 and apertures 410 and 408 along an axis 418. As shown in FIG. 4, the axis 416 is parallel to axis 418. However, it is envisioned that the apertures 404, 406, 408, and 410 may be positioned in various configurations along the surface of housing 402. By way of example, one or more apertures may be included or removed from the apertures as shown in FIG. 4.

Figure 5:
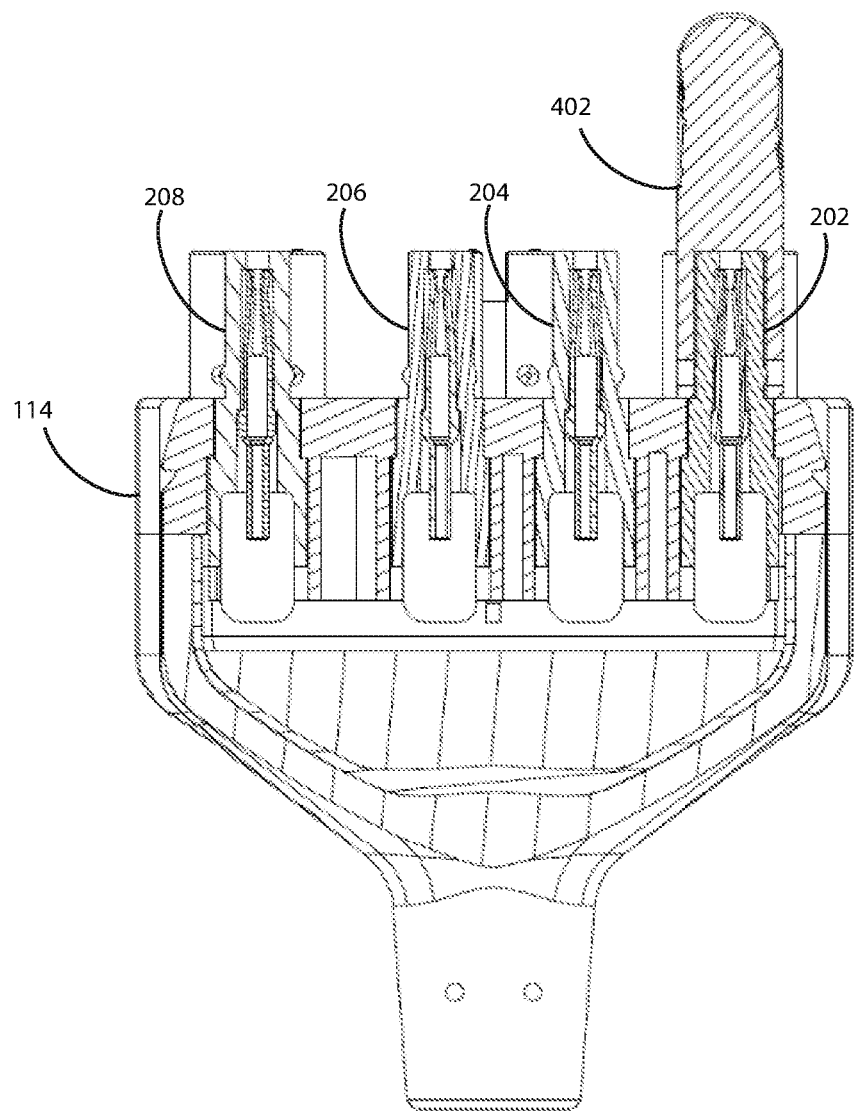
FIG. 5 illustrates a cross-sectional view of the example housing of FIG. 4 coupled to the example extremity hub of FIG. 2 for performing a surgical procedure, according to an embodiment of the present disclosure.

The housing 402 may be attached to or detached to one of the extremity hubs 114, 116, 118, 120, and 122 of FIG. 1. In one example, the housing 402 is attached to a dual connector female receptacle of one of the extremity hubs 114, 116, 118, 120, and 122. By way of example, when the housing 402 is attached to the extremity hub 114, the apertures 406 and 408 are configured to receive the retention elements 216 and 220 of dual connector female receptacle 202 of extremity hub 114 of FIG. 2. Continuing with this example, the apertures 404 and 410 are configured to receive to receive the retention elements 218 and 222 of dual connector female receptacle 202. For example, FIG. 5 illustrates a cross-sectional view of the housing 402 attached to the extremity hub 114 of FIG. 2. The retention elements 216, 218, 220, and 220 of the dual connector female receptacle 202 ensure that an electrical connection is maintained between the electrode of the housing 402 and the extremity hub 114.

Figure 6:
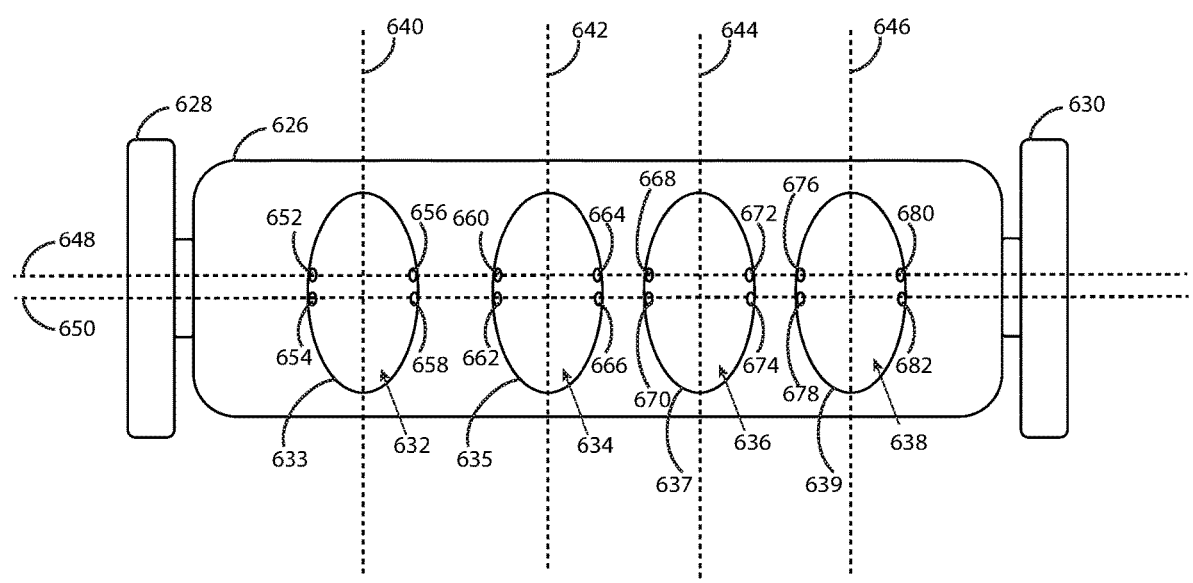
FIG. 6 illustrates an example body for performing a surgical procedure, according to an embodiment of the present disclosure.
Figure 7:
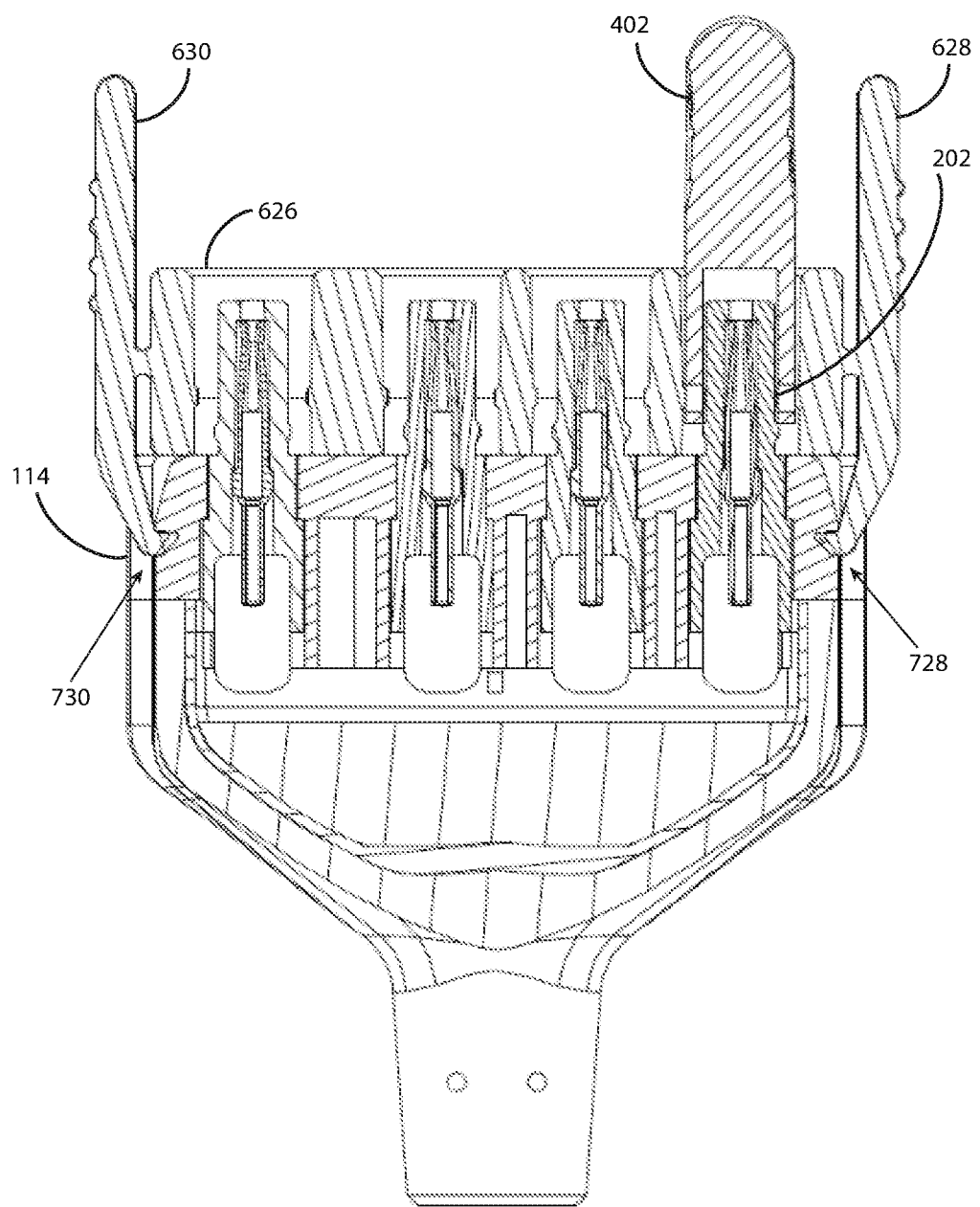
FIG. 7 illustrates the example housing of FIG. 4 coupled to the example body of FIG. 6 for performing a surgical procedure, according to an embodiment of the present disclosure.

FIG. 6 illustrates an example body 626 configured to receive one to four housings (e.g., housing 402). The body 626 includes an aperture 632 located along an axis 640 of the body 626, an aperture 634 located along an axis 642 of the body 626, an aperture 636 located along an axis 644 of the body 626, and an aperture 638 located along an axis 646 of the body 626. Each of the apertures 632, 634, 636, and 638 form corresponding channels 633, 635, 637, and 639 within the body 626. The body 626 includes a first tab 628 coupled to a first surface of the body 626 and a second tab 630 coupled to a second surface of the body 326. As shown in FIG. 6, the first surface is opposite of the second surface. In one example, the first tab 628 and the second tab 630 are configured to attach and detach from an extremity hub (e.g., extremity hubs 114, 116, 118, 120, and 122). For example, FIG. 7 illustrates a cross-sectional view of the housing 402 attached to the body 626. As shown in FIG. 7, the body 626 is attached to the extremity hub 114 of FIG. 2 at a first location 728 via the first tab 628 and a second location 730 via the second tab 630.

Referring back to FIG. 6, the channel 633 formed by the aperture 332 includes retention elements 652 and 654 along a first surface of the channel 633 and retention elements 656 and 658 along a second surface of the channel 633. In one example, the retention elements 652, 654, 656, and 658 are similar to the retention elements (e.g., 216, 218, 220, and 222) of the dual female connector receptacles of the extremity hubs (e.g., extremity hub 114 of FIG. 2, extremity hub 118 of FIG. 3). As shown in FIG. 6, the retention elements 652 and 656 are located along an axis 648. The retention elements 654 and 658 are located along an axis 650. The axis 640 is perpendicular to the axes 648 and 650.

The channel 635 formed by the aperture 634 includes retention elements 660 and 662 along a first surface of the channel 635 and retention elements 664 and 666 along a second surface of the channel 635. Retention elements 660 and 664 are located along the axis 648. Retention elements 662 and 666 are located along the axis 650. The axis 642 is parallel to axis 640 and perpendicular to the axes 648 and 650.

The channel 637 formed by the aperture 636 includes retention elements 668 and 670 along a first surface of the channel 637 and retention elements 672 and 674 along a second surface of the channel 637. Retention elements 668 and 672 are located along the axis 648. Retention elements 670 and 674 are located along the axis 650. The axis 644 is parallel to axis 642 and perpendicular to the axes 648 and 650.

The channel 639 formed by the aperture 638 includes retention elements 676 and 678 along a first surface of the channel 639 and retention elements 680 and 682 along a second surface of the channel 639. Retention elements 676 and 680 are located along the axis 648. Retention elements 678 and 682 are located along the axis 650. The axis 646 is parallel to axis 644 and perpendicular to the axes 648 and 650.

Figure 8:
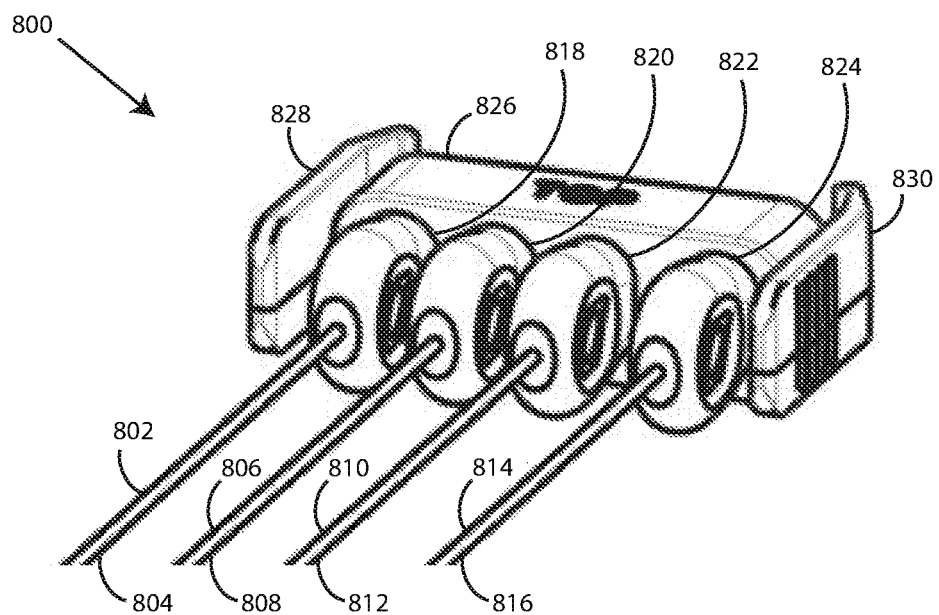
FIG. 8 illustrates an example monitoring cable for performing a surgical procedure, according to an embodiment of the present disclosure.

FIG. 8 illustrates an example monitoring cable 800 that may be attached to or detached from an extremity hub (e.g., extremity hubs 114, 116, 118, 120, and 122). The monitoring cable 800 includes electrode wires 802, 804, 806, 808, 810, 812, 814, and 816, housings 818, 820, 822, and 824, and body 826. In one example, the housings 818, 820, 822, and 824 are configured as the housing 402 of FIG. 4. In one example, the body 826 is configured as the body 626 of FIG. 6.

Prior to commencing a surgical procedure, the electrode wires 802, 804, 806, 808, 810, 812, 814, and 816 are configured to monitor various parts of a patient's body. In one example, in surgical procedure that involves a portion of the cervical spine, the electrodes associated with electrode wires 802 and 804 may be placed at the trapezius, the electrodes associated with electrode wires 806 and 808 may be placed at the triceps, the electrodes associated with electrode wires 810 and 812 may be placed at the abductor pollicis *brevis* and the abductor digiti minimi, and the electrodes associated with electrode wires 814 and 816 at the deltoid. In another example, in a surgical procedure that involves a portion of the lumbar spine, the electrodes associated with electrode wires 802 and 804 may be placed at the vastus medialis, the electrodes associated with electrode wires 806 and 808 may be placed at the biceps femoris, the electrodes associated with electrode wires 810 and 812 may be placed at the gastroc medial, and the electrodes associated with electrode wires 814 and 816 at the tibialis anterior.

Figure 9:
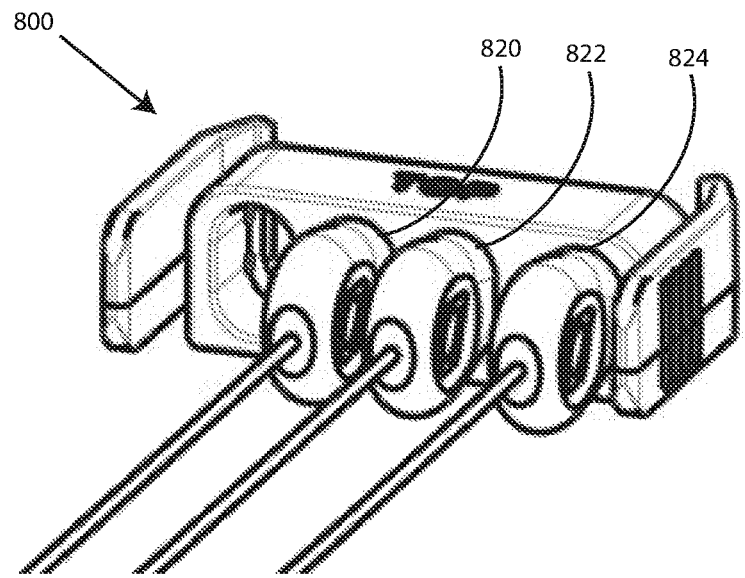
FIG. 9 illustrates the example monitoring cable of FIG. 8 for performing a surgical procedure, according to an embodiment of the present disclosure.

Housings 818, 820, 822, and 824 are configured to receive a first end of a first electrode wire and a first end of a second electrode wire. The housings 818, 820, 822, and 824 are also configured to attach to and detach from the body 826. For example, as shown in FIG. 9, housing 818 has been detached from the body 826 while housings 820, 822, and 824 are shown attached to the body 826. The ability to remove a single housing from the body 826 while allowing the other housings to remain connected to the body 826 helps to reduce the time necessary to prepare a patient for a surgical procedure. In one scenario, a user may receive an alert via monitoring system (not shown) coupled to the harness 100 that indicates a problem with the electrodes associated with electrode wires 802 and 804 corresponding to housing 818. In this scenario, the user may choose to remove only housing 818 and replace it with another housing without having to take the time to replace all the other electrodes and corresponding housings.

Referring back to FIG. 8, the body 826 includes a first tab 828 coupled to a first surface of the body 826 and a second tab 830 coupled to a second surface of the body 826. As shown in FIG. 8, the first surface is opposite of the second surface. In one example, the first tab 828 and the second tab 830 are configured to attach and detach from an extremity hub (e.g., extremity hubs 114, 116, 118, 120, and 122).

Figure 10:
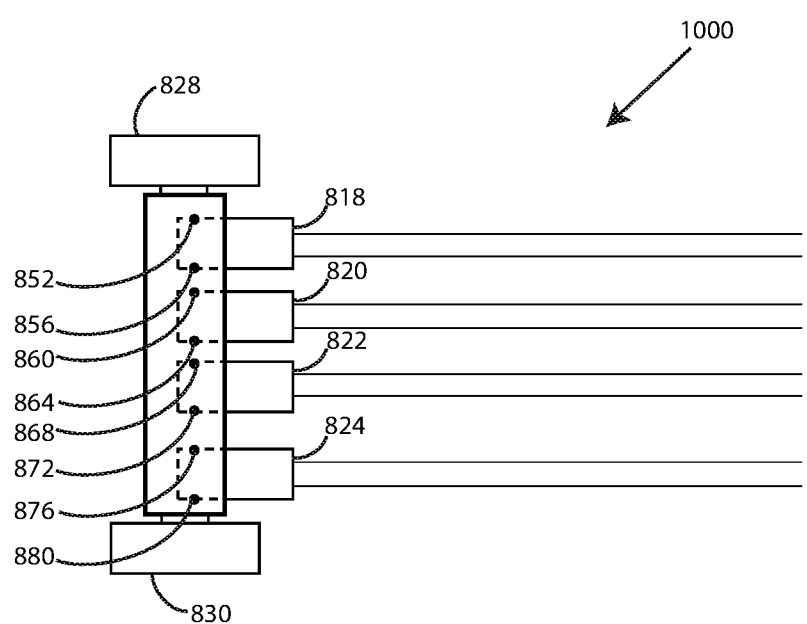
FIG. 10 illustrates an example monitoring cable for performing a surgical procedure, according to an embodiment of the present disclosure.

FIG. 10 illustrates a top view of a monitoring cable 1000. In one example, the monitoring cable 1000 is similar to the monitoring cable 800 of FIG. 8. As shown in FIG. 10, the body 826 is configured to slidably receive housings 818, 820, 822, and 824. The housings 818, 820, 8322, and 824 are held in a fixed position based on insertion of the retention elements 852, 856, 860, 864, 868, 872, 876, and 880 within apertures (e.g., apertures 402, 406, 408, and 410 of housing 402 of FIG. 4) of housings 818, 820, 822, and 824.

Figure 11:
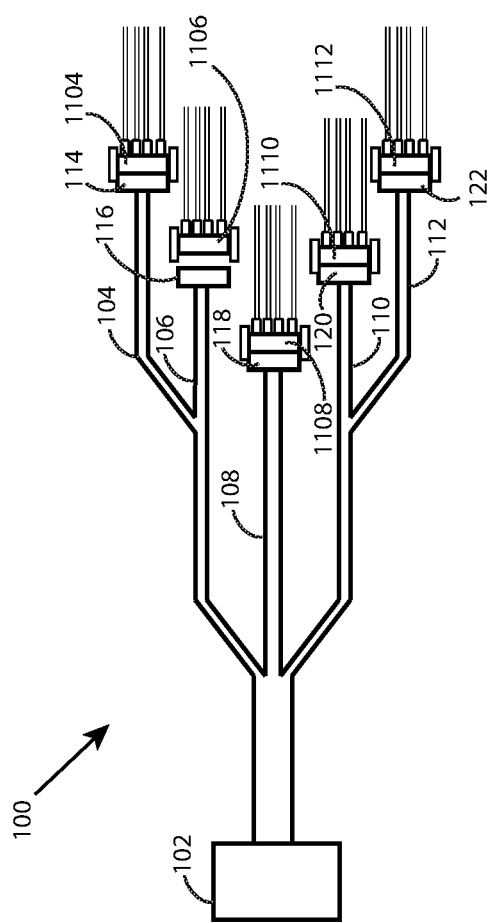
FIG. 11 illustrates the example harness of FIG. 1 and example monitoring cables for performing a surgical procedure, according to an embodiment of the present disclosure.

FIG. 11 illustrates the harness 100 of FIG. 1 coupled to monitoring cables 1104, 1108, 1110, and 1112 and not coupled to monitoring cable 1106. In one example, the monitoring cables 1104, 1106, 1108, 1110, and 1112 are similar to the monitoring cable 800 of FIG. 8 and the monitoring cable 1000 of FIG. 10. As shown in FIG. 11, the monitoring cables 1104, 1106, 1108, 1110, and 1112 are configured to attach and detach from the extremity hubs 114, 116, 118, 120, and 122 in a manner as described above.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

What is claimed is:

1. A harness comprising:
a patient module connector;
an extremity hub;
a branch including a plurality of channel pairs, wherein the branch includes a first end coupled to the patient module connector and a second end coupled to the extremity hub; and
a monitoring cable configured to attach and detach from the extremity hub, wherein the monitoring cable includes:
a first electrode wire;
a second electrode wire;
a housing configured to receive a first end of the first electrode wire and a first end of the second electrode wire, wherein the housing includes a first aperture and a second aperture along an axis of the housing; and
a body that includes a channel formed by an aperture along a first axis of the body, wherein the channel includes (i) a first retention element located on a first surface of the channel and along a second axis of the body and (ii) a second retention element located along a second surface of the channel and along the second axis, wherein the first axis and the second axis are perpendicular, wherein the body is configured to slidably receive the housing and hold the housing in a fixed position based on insertion of the first retention element within the first aperture and insertion of the second retention element within the second aperture.

2. The harness of claim 1, further comprising:
a first tab coupled to a first surface of the body; and
a second tab coupled to a second surface of the body, wherein the first surface is opposite of the second surface, wherein the first tab and the second tab are configured to attach and detach from the extremity hub.

3. The harness of claim 1, wherein the plurality of channel pairs include a plurality of channel pairs for acquiring a stimulation signal and a plurality of channel pairs for providing a stimulation pair.

4. The monitoring cable of claim 1, wherein the patient module connector comprises a programmable memory device.

5. The harness of claim 1, wherein the channel includes (i) a third retention element located on the first surface of the channel and along a third axis of the body and (ii) a fourth retention element located along the second surface of the channel and along the third axis, wherein the third axis is parallel to the second axis.

6. The harness of claim 5, wherein the housing includes a third aperture and a fourth aperture along a second axis of the housing, wherein the second axis of the housing is parallel the axis of the housing, wherein the housing is additionally held in the fixed position based on insertion of the third retention element within the third aperture and insertion of the fourth retention element within the fourth aperture.

7. The harness of claim 1, wherein the body further includes a second channel formed by a second aperture along a third axis of the body, wherein the third axis and the first axis are parallel, wherein the second channel includes (i) a first retention element located on a first surface of the second channel and along a fourth axis of the body and (ii) a second retention element located along a second surface of the second channel and along the fourth axis, wherein the fourth axis and the third axis are perpendicular.

8. The harness of claim 7, wherein the body further includes a third channel formed by a third aperture along a fifth axis of the body, wherein the fifth axis and the first axis are parallel, wherein the third channel includes (i) a first retention element located on a first surface of the third channel and along a sixth axis of the body and (ii) a second retention element located along a second surface of the third channel and along the sixth axis, wherein the sixth axis and the fifth axis are perpendicular.

9. The harness of claim 8, wherein the body further includes a fourth channel formed by a fourth aperture along a seventh axis of the body, wherein the seventh axis and the first axis are parallel, wherein the fourth channel includes (i) a first retention element located on a first surface of the fourth channel and along a eighth axis of the body and (ii) a second retention element located along a second surface of the fourth channel and along the sixth axis, wherein the sixth axis and the fifth axis are perpendicular.

10. The harness of claim 1, wherein the extremity hub includes a third retention element and a fourth retention element, wherein the extremity hub is configured to receive the housing and hold the housing in a fixed position based on insertion of the third retention element within the first aperture and insertion of the fourth retention element within the second aperture.

11. The harness according to claim 1, further comprising:
a plurality of electrode wires including the first electrode wire and the second electrode wire;
a plurality of housings including the housing configured to receive the first end of the first electrode wire and the second end of the second electrode wire, configured to receive the plurality of electrode wires, wherein the plurality of housings includes a plurality of first apertures including the first aperture; and
the body including a plurality of channels formed by a plurality of second apertures along the body including the second aperture, wherein the plurality of channels include a plurality of retention elements located on surfaces of the plurality of channels including the first retention element and the second retention element, wherein the body is configured to slidably receive the plurality of housings and hold the plurality of housings in fixed positions based on insertion of the plurality of retention elements within the plurality of first apertures.

12. The harness of claim 1, wherein the patient module connector comprises a programmable memory device, and wherein the plurality of channel pairs includes a plurality of channel pairs for acquiring a stimulation signal and a plurality of channel pairs for providing a stimulation pair.

* * * * *